(12) United States Patent
Kuntz et al.

(10) Patent No.: US 10,238,789 B2
(45) Date of Patent: Mar. 26, 2019

(54) IRRIGATION/ASPIRATION SYSTEM, CARTRIDGE, PUMP UNIT, SURGICAL MACHINE, METHOD FOR CONTROLLING

(71) Applicant: D.O.R.C. Dutch Ophthalmic Research Center (International) B.V., Zuidland (NL)

(72) Inventors: John Peter Kuntz, Zuidland (NL); Gerrit Jan Vijfvinkel, Zuidland (NL)

(73) Assignee: D.O.R.C. Dutch Ophthalmic Research Center (International) B.V., Zuidland (NL)

( * ) Notice: Subject to any disclaimer, the term of this patent is extended or adjusted under 35 U.S.C. 154(b) by 15 days.

(21) Appl. No.: 14/426,356

(22) PCT Filed: Sep. 6, 2013

(86) PCT No.: PCT/NL2013/050645
§ 371 (c)(1),
(2) Date: Mar. 5, 2015

(87) PCT Pub. No.: WO2014/038941
PCT Pub. Date: Mar. 13, 2014

(65) Prior Publication Data
US 2015/0250939 A1    Sep. 10, 2015

(30) Foreign Application Priority Data

Sep. 6, 2012    (NL) ..................... 2009424

(51) Int. Cl.
*A61M 3/02*    (2006.01)
*A61M 1/00*    (2006.01)
*A61F 9/007*   (2006.01)

(52) U.S. Cl.
CPC ....... *A61M 3/0258* (2013.01); *A61F 9/00745* (2013.01); *A61M 1/0031* (2013.01);
(Continued)

(58) Field of Classification Search
CPC ............ A61M 1/0058; A61M 2205/12; A61M 2205/3337; A61M 2205/3341; A61M 3/0283
(Continued)

(56) References Cited

U.S. PATENT DOCUMENTS 4,236,880 A * 12/1980 Archibald ......... A61M 5/14224
                                                    138/30
5,499,969 A *  3/1996 Beuchat ............... A61M 1/0058
                                                    128/DIG. 12
(Continued)

FOREIGN PATENT DOCUMENTS

WO    2010/129128 A1    11/2010
WO    2011/063794 A1     6/2011

OTHER PUBLICATIONS

International Search Report and Written Opinion dated Oct. 25, 2013 for PCT/NL2013/050645.

*Primary Examiner* — Deanna K Hall
(74) *Attorney, Agent, or Firm* — Knobbe, Martens, Olson & Bear, LLP

(57) ABSTRACT

An irrigation/aspiration system for irrigating and aspirating a surgical site includes an irrigation flow path for directing fluid towards the surgical site via an irrigation connection, and an aspiration flow path for directing fluid away from the surgical site via an aspiration connection. A membrane pump is arranged for pumping fluid through the irrigation flow path and/or the aspiration flow path. The membrane pump includes a main pump chamber, at least two valves for opening and/or closing the main pump chamber and an auxiliary pump chamber arranged between the irrigation connection and/or aspiration connection and the main pump chamber for compensating movement of a main pump plunger element in the main pump chamber to provide for an
(Continued)

approximately even fluid flow to and/or from the surgical site.

13 Claims, 7 Drawing Sheets

(52) U.S. Cl.
CPC ........ *A61M 1/0058* (2013.01); *A61M 1/0072* (2014.02); *A61M 3/0283* (2013.01); *A61M 2205/12* (2013.01); *A61M 2205/3331* (2013.01); *A61M 2205/3334* (2013.01); *A61M 2205/3337* (2013.01); *A61M 2205/3341* (2013.01); *A61M 2210/0612* (2013.01)

(58) Field of Classification Search
USPC .................................................. 604/30, 131
See application file for complete search history.

(56) References Cited

U.S. PATENT DOCUMENTS

| 8,692,167 B2 * | 4/2014 | Hedmann | A61M 1/28 219/494 |
|---|---|---|---|
| 2004/0059284 A1 | 3/2004 | Nash et al. | |
| 2007/0112297 A1 | 5/2007 | Plahey | |

\* cited by examiner

IRRIGATION/ASPIRATION SYSTEM, CARTRIDGE, PUMP UNIT, SURGICAL MACHINE, METHOD FOR CONTROLLING

CROSS REFERENCE TO RELATED APPLICATIONS

This application is the U.S. National Phase of International Application No. PCT/NL2013/050645, filed Sep. 6, 2013, designating the U.S. and published in English as WO 2014/038941 on Mar. 13, 2014 which claims the benefit of Netherlands Patent Application No. 2009424, filed Sep. 6, 2012.

FIELD OF THE INVENTION

The invention relates to an irrigation/aspiration system for irrigating and aspirating a surgical site.

DESCRIPTION OF THE RELATED ART

Irrigation/aspiration systems are known and are used during small incision surgery, in particular during ophthalmic surgery. The irrigation/aspiration system is arranged for directing fluid towards and from the eye during the surgery. The system is used for irrigation and aspiration of the eye and to maintain a controlled intraocular pressure in the eye during the surgery.

The irrigation/aspiration system typically comprises a pump for pumping the fluid to and/or from the surgical site. The pumps are usually arranged at the aspiration side of the system, but can also be arranged in the irrigation side of the system. In the prior art, typically, two pump systems are known, i.e. either a pressure controlled pump or a flow controlled pump. Both pump systems have advantages and drawbacks.

A pressure controlled system typically comprises a vacuum pump or a venturi pump. An advantage of the pressure controlled pump is that the pressure, i.e. the underpressure or vacuum, in the system is well known. Also, the quick response time of the pressure controlled pump is highly appreciated. A drawback of the pressure controlled pump is that flow information is not available. Flow is a result of the vacuum applied and the resistance in the flow path, and a precise flow is difficult to control.

A flow controlled system typically comprises a peristaltic pump. An advantage of the flow controlled system is the relatively stable flow rate. Another advantage is the stable flow, independent of the viscosity of the medium. During eye surgery the eye may be filled with a combination of air and liquid. The fluids may be of different viscosity. When using the vacuum pump of the pressure controlled system, the resulting flow will be different in air or water. A drawback of the existing flow controlled systems is the relatively slow response time and/or the fluctuations in the flow due to the peristaltic movement of the pump.

Therefore, typically either a pressure controlled pump or a flow controlled pump is used to operate in either a pressure controlled mode or a flow controlled mode. It is also known to provide a combined system that has both pumps, a flow controlled pump and a pressure controlled pump, as for example described in EP 1 900 347. A drawback of such a system however is, that two separate pumps are required, resulting in a relatively voluminous apparatus. Further, switching between the pressure controlled mode and the flow controlled mode can be relatively complex and takes time.

SUMMARY

There is a need for an irrigation/aspiration system that obviates at least one of the above mentioned drawbacks. For example, there is a need for an irrigation/aspiration system that allows operating in the flow controlled mode or the pressure controlled mode while maintaining the advantages of either control mode.

Thereto, the invention provides for an irrigation/aspiration system for irrigating and aspirating a surgical site comprising an irrigation flow path for directing fluid towards the surgical site via an irrigation connection, and an aspiration flow path for directing fluid away from the surgical site via an aspiration connection, wherein in the irrigation flow path and/or the aspiration flow path a membrane pump is arranged for pumping fluid through the irrigation flow path and/or the aspiration flow path, wherein the membrane pump comprises a main pump chamber, at least two valves for opening and/or closing the main pump chamber and an auxiliary pump chamber arranged between the irrigation connection and/or aspiration connection and the main pump chamber for compensating movement of a main pump plunger element in the main pump chamber to provide for an approximately smooth flow to and/or from the surgical site.

By providing a membrane pump comprising a main pump chamber and an auxiliary pump chamber that is arranged between the main pump chamber and the surgical site, the pulsating movement of the main pump plunger element in the main pump chamber can be compensated by the movement of an auxiliary plunger element in the auxiliary pump chamber such that an approximately smooth flow to/from the surgical site can be obtained.

By moving a main pump plunger element in the main pump chamber up and down, a pulsation fluid flow is obtained. The flow can be known and is dependent on the velocity of the plunger element. The main pump chamber then functions as a flow controlled pump alike a peristaltic pump, generating a pulsation fluid flow. By adding the auxiliary pump chamber to the main pump chamber of which an auxiliary pump plunger element can compensate the movement of the main pump plunger element, an approximately nearly smooth flow can be obtained, which is an improvement with respect to the known flow controlled pumps. By providing the auxiliary pump chamber the membrane pump can be operated in a flow controlled mode and generating a nearly smooth flow, as opposed to the pulsating flow of the conventional peristaltic pumps. Since the flow rate is known, because the flow rate depends on the velocity of the plunger elements, the membrane pump can be operated as a flow controlled pump. Further, by providing a system according to the invention, the flow can be stable and independent of the viscosity of the fluid.

In the context of the invention, an approximately smooth flow is understood to be a nearly smooth flow, i.e. a flow with a nearly even flow rate. An approximately or nearly smooth flow is understood to have no or limited flow rate variations, as opposed to a pulsating flow of prior art flow controlled pumps, such as peristaltic pumps. Advantageously, the flow obtained by a pump system according to the invention is free of waves or pulses, as opposed to the flow of a conventional peristaltic pump which is inherently a wave flow or pulsating flow.

In addition, by providing a membrane pump with a main pump chamber and an auxiliary pump chamber, the flow of the membrane pump can be relatively quickly adapted by adapting the movement of the plunger elements. The response time of the membrane pump according to the invention can therefore be relatively short compared to the response time of conventional flow controlled pumps, such as a peristaltic pump.

Advantageously, a control unit is provided to control the operation of the membrane pump, in particular to control the movement of the plunger elements and/or the valves. It is possible to provide for a mechanical control system, for example by providing the plunger elements and/or valve elements on a camshaft the velocity of which can be varied to provide for a higher or lower flow. Also, the cams on the camshaft can be made velocity-dependent.

Alternatively, each plunger element and/or valve element may be operated individually by, for example, a direct drive motor. By providing a control unit that controls the direct drive motors, the plunger and/or valve elements can be operated individually in velocity and position such that the flow can be optimally and relatively accurately controlled.

By providing a pressure sensor that is adapted to establish the pressure in the system, the pressure can be known. When the pressure value is known, the pressure can be used as a control parameter and it may become possible to operate the system as a pressure controlled system.

When the pressure is known, and the flow in the system is known as well, the system can be controlled on the pressure and/or on the flow, so it can be operated as a pressure controlled system or as a flow controlled system having the advantages of an approximately smooth flow and of a relatively quick response time.

In a pressure controlled mode, the pressure value can be used as an input to the control unit that may adapt the control of the plunger and/or valve elements depending on the desired pressure value.

During a surgical procedure, the surgeon may like to use the system in a first step in a pressure controlled mode and in a second step in a flow controlled mode. For example, in the first step eye fluid may be removed relatively fast from the eye using maximum flow and pressure control. In the second step, the flow may be limited and control of the flow becomes important, for example when approaching the retina. When using the system according to the invention, a relatively simple switch between the flow controlled mode and the pressure controlled mode is possible, complex switching mechanisms between two separate pumps can be obviated. In addition, when using the pump according to the invention, the flow and the pressure in the system may be known, allowing relatively accurate operating and controlling of the pump. Furthermore, by using a membrane pump according to the invention, a relatively quick response time can be obtained.

It is understood that a pump system comprising a main pump chamber with a main pump plunger element with at least two valves for opening and/or closing of the main pump chamber, further comprising an auxiliary pump chamber with an auxiliary pump plunger element that is at one side in fluid connection with the main pump chamber, wherein the auxiliary pump plunger element is arranged to compensate movement of the main pump plunger element to provide for an approximately even fluid flow at a side of the auxiliary pump chamber opposite the main pump chamber can be considered as an invention on its own. By providing an auxiliary pump chamber with an auxiliary pump plunger element, the pulsating movement of the main pump chamber can be compensated such that an approximately even flow can be obtained as compared to the pulsating flow of the main pump chamber. The auxiliary pump plunger element moves in antiphase with respect to the main pump plunger element as to obtain the compensating movement and the approximately even flow.

In another aspect of the invention, the membrane pump comprises plunger elements that are arranged to provide an underpressure between a membrane body and a plunger element. By providing an underpressure, also called vacuum pressure, between the membrane body and the plunger element, the membrane body is sucked against the plunger element. When moving the plunger element, the membrane body is moved as well and the pump chamber can thus become larger or smaller.

It is understood that the aspect of a plunger element providing an underpressure between the plunger element and the membrane body such that the membrane body is sucked against the plunger element, can be considered as an invention on its own. Contrary to a prior art membrane pump in which the membrane is moved by the pushing action of a plunger against the membrane, the membrane is now moved by the plunger element due to suction contact between the plunger element and the membrane. According to this aspect of the invention, the membrane body is sucked against the plunger element and is thus, during operation, in permanent contact with the plunger element. Movement of the plunger element causes movement of the membrane body. This allows a more accurate control of the movement of the membrane body and thus of the volume of the pump chamber.

To provide an underpressure or vacuum between the plunger element and the membrane body, the plunger element may be provided with a hollow bore or channel that that ends in an underside of the plunger element facing the membrane body. By providing an underpressure through the bore or channel, the membrane body is sucked against the underside of the plunger element. The underpressure between the plunger element and the membrane body is relatively high, for example the absolute pressure may be between approximately 15-75 mmHg, preferably approximately between 20-60 mmHg. Such a relatively low pressure is also referred to as a vacuum pressure. Advantageously, the irrigation/aspiration system comprises a cartridge in which the irrigation flow path and the aspiration flow path are arranged and a pump unit for cooperation with the cartridge. By providing a cartridge and a pump unit, a modular system can be obtained. The cartridge can be provided as a one-way or throw-away article, while the pump unit may be of a more permanent nature, for example arranged in a surgical operating machine. By providing a cartridge, the cartridge can be made relatively easily sterile, such that the flow paths in the cartridge can be sterile as well.

Advantageously, the flow paths in the cartridge are rigid in which the membrane bodies are arranged. Contrary to the rigid flow paths, the membrane bodies are flexible. This is also contrary to a prior art peristaltic pump or prior art cassette for a peristaltic pump that usually requires at least part of the flow path to be flexible that is in engagement with the peristaltic pump.

According to an aspect of the invention, the surgical cartridge comprises an inner plate and an outer plate arranged approximately parallel to the inner plate, wherein between the inner plate and the outer plate flow paths are arranged forming an irrigation flow path for directing fluid towards the surgical site via an irrigation connection and an aspiration flow path for directing fluid away from the surgical site via an aspiration connection, wherein the inner plate comprises membrane bodies adapted for cooperation with plunger elements and/or valve elements of a membrane pump unit, wherein the membrane bodies comprise a main membrane body, at least two valve membrane bodies and an auxiliary membrane body adapted to cooperate with a main membrane plunger element, valve elements and an auxiliary membrane plunger element of the pump unit respectively.

By providing the flow paths in the cartridge, the flow paths are determined and the cartridge is relatively fast ready to use. Only the irrigation line and the aspiration line need to be connected to the irrigation connection and the aspiration connection to obtain a connection to and from the surgical site. The inner plate and the outer plate may be of relatively hard plastic parts that may be welded together to form closed channels, the fluid flow path, and chambers. At some positions, a wall part of the channels and/or chambers is made of an elastic material forming a membrane.

In addition, by providing an inner plate in which the membrane bodies are arranged, the cooperation with the pump unit can be relatively easily be established. By coupling the cartridge to the pump unit, the plunger and/or valve elements of the pump unit are facing their respective membrane bodies. This allows for easy manipulating of the cartridge to the pump unit. Furthermore, the thus obtained irrigation/aspiration is less sensitive to fabrication tolerances of the cartridge.

In an advantageous embodiment, the cartridge is provided with a sealing edge for sealingly coupling to the pump unit. The sealing edge encloses the inner plate and by coupling the cartridge to the pump unit, the sealing edge seals of the chamber between the inner plate and the pump unit. By sealingly coupling the cartridge to the pump unit, the chamber between the inner plate and the pump unit can be put at an underpressure to suck the cartridge against the pump unit. This is also known as 'vacuum clamping' the cartridge to the pump unit. Preferably, the underpressure in the chamber between the inner plate and the pump unit is maintained during the use of the cartridge on the pump unit to provide for a firm coupling of the cartridge to the pump unit. Due to the vacuum clamping, a firm contact between the hard inner plate of the cartridge and the pump unit may be established which may increase actuation accuracy.

Typically, the cartridge may in addition be provided with coupling elements, such as click fingers, or hooks, or pins or ratchets, etc. to initially couple with the pump unit as well to provide for additional safety. During use, the cartridge will first be coupled to the pump unit by means of the coupling elements. Then, the cartridge is already well positioned and centred in front of the pump unit. Secondly, an underpressure will be provided between the cartridge and the pump unit to sealingly suck the cartridge to the pump unit. Therefore, also in case of a power breakdown, when the vacuum falls away, the cartridge remains coupled to the pump unit by means of the coupling elements.

According to another aspect of the invention, the pump unit comprises plunger elements and valve elements for cooperation with membrane bodies to provide for a membrane pump, wherein the plunger elements comprise a main plunger element and an auxiliary plunger element for cooperation with a main membrane body and an auxiliary membrane body respectively.

According to another aspect of the invention, the pressure sensor can be provided as sensor external to the cartridge cooperating with a membrane on the cartridge.

In a cartridge, fluid paths are arranged and in a wall of such a fluid path, a membrane can be provided. The membrane typically is relatively thin and flexible, one side of the membrane is at the inner side of the fluid flow path and an other side of the membrane is at the outer side of the fluid flow path. Preferably, the membrane is arranged in a side wall of the flow path. Thus, the side of the membrane inside the fluid flow path, i.e. the inner side of the membrane, is in contact with the fluid. The other side of the membrane outside the fluid flow path, i.e. the outer side of the membrane is not in contact with the fluid. According to this aspect of the invention, a pressure sensor is now provided that cooperates with the outer side of the membrane. The pressure sensor then measures the pressure of the fluid on the membrane. Therefore, the pressure sensor itself external to the cartridge and is not in contact with the fluid. The membrane is very compliant compared to the pressure sensor and has therefore no significant influence on the pressure measurement inside the cartridge.

This is contrary to the prior art pressure measurements. According to the prior art, the cartridge itself is provided with a pressure sensor that is arranged partially inside the fluid flow path of the cartridge. Thus, the pressure sensor is in contact with fluid, which requires complex and expensive sealing. Also, the cartridge is a throw-away disposable article, such that, when disposing the cartridge, the pressure sensor is thrown away as well. This results in a relatively expensive cartridge.

By providing the pressure sensor outside the cartridge, e.g. in the pump unit or on the operating machine, the pressure sensor can cooperate with a membrane in the fluid flow path of the cartridge. This may result in a more cost effective manufacturing of the cartridge, since it can be provided without the pressure sensor. Also, since the pressure sensor on the cartridge is now absent, the cartridge can become thinner, thereby reducing packaging, storage and transport costs. Furthermore, the pressure sensor itself may be of a more cost effective type, since the pressure sensor is not in contact with fluid.

Advantageously, the pressure sensor is a load cell sensor measuring the displacement of the membrane and translating this displacement into a force or pressure load.

This aspect of the pressure sensor can be considered as an invention on its own.

The invention further relates to a surgical operating machine comprising a pump unit.

The invention also relates to a method for operating an irrigation/aspiration system, wherein the auxiliary pump chamber is operated in antiphase with respect to the main pump chamber to provide for an approximately smooth flow.

By moving the main plunger element up and down, fluid is pumped through the flow path in a pulsating way. When the main pump chamber is filled, an inlet valve closes and an outlet valve of the main pump chamber opens to allow the fluid to flow away due to the downwards movement of the main pump plunger element. In the mean time the auxiliary pump plunger takes over the flow task by moving upwards. After emptying the main pump chamber, the outlet valve closes and the inlet valve opens again, and the main pump plunger element moves up to allow filling the main pump chamber. When the main pump plunger element moves upwards, the auxiliary pump plunger element moves downward. The auxiliary pump plunger element and the main pump plunger element therefore operate in antiphase to compensate for the fluctuations of the main pump plunger element, such that an approximately smooth flow is obtained, such that there is an approximately smooth flow to and/or from the surgical site.

Further advantageous embodiments are represented in the subclaims.

BRIEF DESCRIPTION OF THE DRAWINGS

The invention will further be elucidated on the basis of exemplary embodiments which are represented in the drawings. The exemplary embodiments are given by way of non-limitative illustration of the invention.

In the drawings.

DETAILED DESCRIPTION OF CERTAIN EMBODIMENTS

Figure 1D:
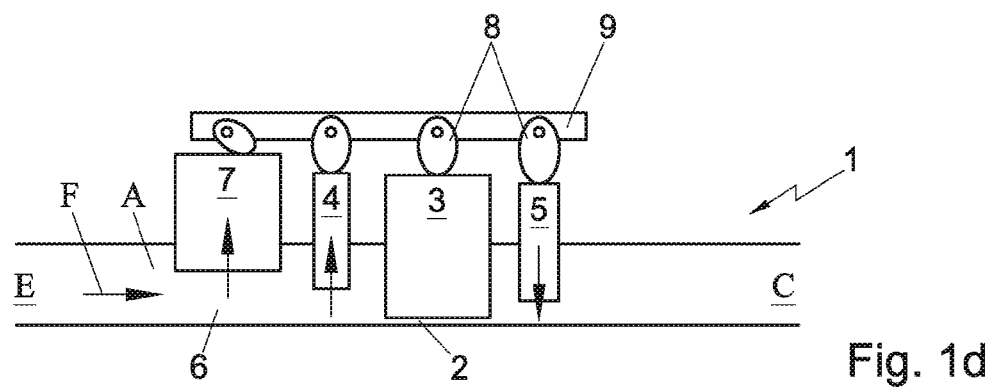
FIG. 1 shows a schematic representation in four steps of the operation of the membrane pump according to the invention.

It is noted that the figures are only schematic representations of embodiments of the invention that are given by way of non-limiting example. In the figures, the same or corresponding parts are designated with the same reference numerals.

FIG. 1 shows a schematic representation of a pump 1 according to the invention. The pump 1 is here arranged in an aspiration flow path A of an irrigation/aspiration system. In the aspiration flow path A, the fluid comes from the eye E and goes to a collection bag C. It is evident that the pump 1 can also be arranged in an irrigation flow path.

Pump 1 comprises a main pump chamber 2 with a main pump plunger element 3. The main pump chamber 2 can be opened and closed by a first valve 4 and a second valve 5. Upstream of the main pump chamber 2, an auxiliary pump chamber 6 is arranged with an auxiliary pump plunger element 7. In this embodiment, the main and auxiliary pump plunger elements 3, 7 and the first and second valves 4, 5 are operated by cams 8 on a camshaft 9.

The operation of the pump 1 will now be elucidated using four figures FIG. 1a-FIG. 1d each depicting one step. It may be clear that the movement of the plunger elements 3, 7 and of the valves 4, 5 is approximately continuous and more or less steps may be visualized.

Figure 1A:
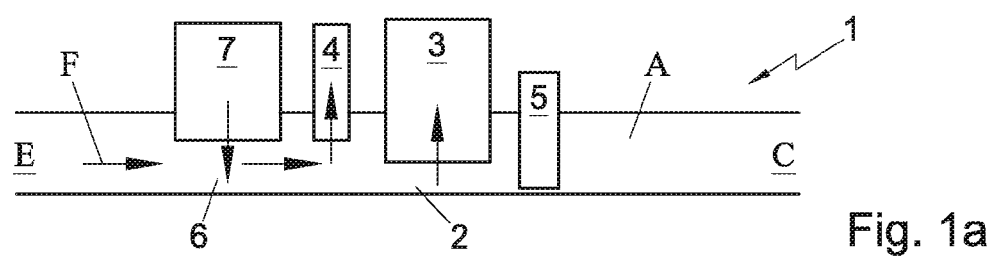

In a first step, shown in FIG. 1a, the main pump plunger element 3 moves upwardly, thereby pumping fluid out of the eye E towards the auxiliary pump chamber 6 and main pump chamber 2 while the valve 4 is open. The second valve 5 is closed. Simultaneously, the auxiliary pump plunger element 7 moves downwardly and so decreasing the amount of volume. However, the auxiliary pump plunger element 7 moves slower than main pump plunger element 3 resulting in a smooth flow out of the eye. At the end of this step, the main pump chamber 2 is now maximally filled with fluid, while the auxiliary pump chamber 6 is almost empty.

Figure 1B:
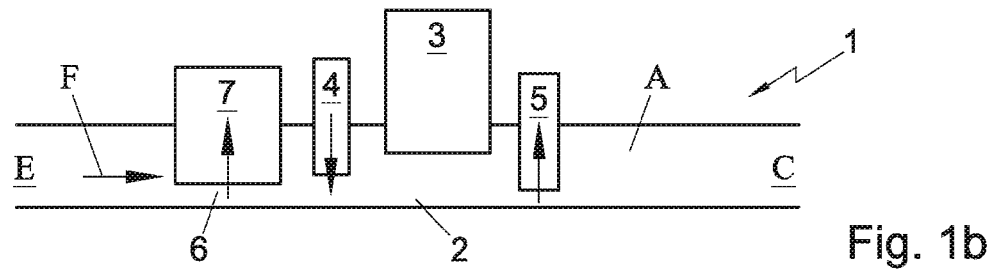

In step 2, as shown in FIG. 1b, the first valve 4 is closed, and the second valve 5 is opened. The auxiliary pump plunger 7 is moving upwards, generating an aspiration flow towards the auxiliary pump chamber 6.

Figure 1C:
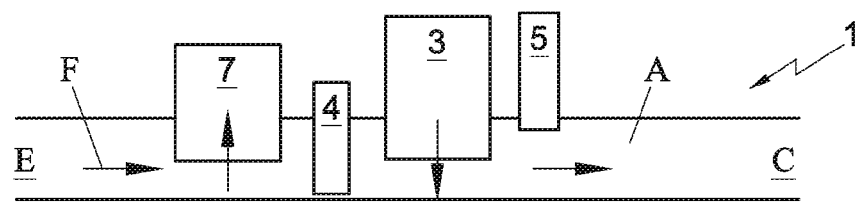

In step 3, as shown in FIG. 1c, by moving the main pump plunger element 3 downwardly, fluid is pumped out of the main pump chamber 3 towards the collection bag C. This releasing of the fluid into the aspiration flow path A towards the collection bag C is done in a pulsating movement. This is however not a problem, since this released fluid goes to the collection bag C. In the mean time, the auxiliary pump plunger 7 is moving upwards, generating an aspiration flow towards the auxiliary pump chamber 6. At the end of this step, the main pump chamber 3 is empty.

In step 4, as shown in FIG. 1d, the second valve 5 is closed, and the first valve 4 is opened. The auxiliary pump plunger 7 is moving upwards, generating an aspiration flow towards the auxiliary pump chamber 6.

Due to the provision of auxiliary pump chamber 6 with auxiliary pump plunger 7, the pulsating flow of the main pump chamber 2 can be compensated, such that fluid is aspirated out of the eye E in a nearly even volume. The auxiliary pump plunger element 7 in fact compensates the movement of the main pump plunger element 3 and thus an almost smooth fluid flow aspirated out of the eye E can be obtained. The compensating movement of the auxiliary pump plunger element 7 is obtained by moving the auxiliary pump plunger element 7 in antiphase with respect to the main pump plunger element 3.

By varying the velocity of the camshaft 9, the fluid flow F can be varied as well. Also, the cams 8 can be made velocity-dependent.

Alternatively to the cams 8 and the camshaft 9, the plunger elements 3, 7 and the valves 4, 5 can be controlled individually and independently from each other, for example when using direct drive motors. Then, each plunger element 3, 7 and each valve 4, 5 is controlled by its own direct drive motor.

The pump 1 according to the invention therefore not only provides for a quick response time, but also provides for an approximately even fluid flow F out of the eye E. By varying the velocity of the camshaft 9, the velocity of the plunger elements 3, 7 and valves 4, 5 is adjusted instantaneously, providing for a quick response time. Also when using direct drive motors, varying the rpm of a direct drive motor instantaneously influences the movement of the respective plunger and/or valve body. Further, by providing the auxiliary pump chamber 6 with the auxiliary pump plunger element 7, the fluid flow F can become approximately even, i.e. substantially without pulsations, as compared to the fluid flow of e.g. a peristaltic pump.

Figure 2:
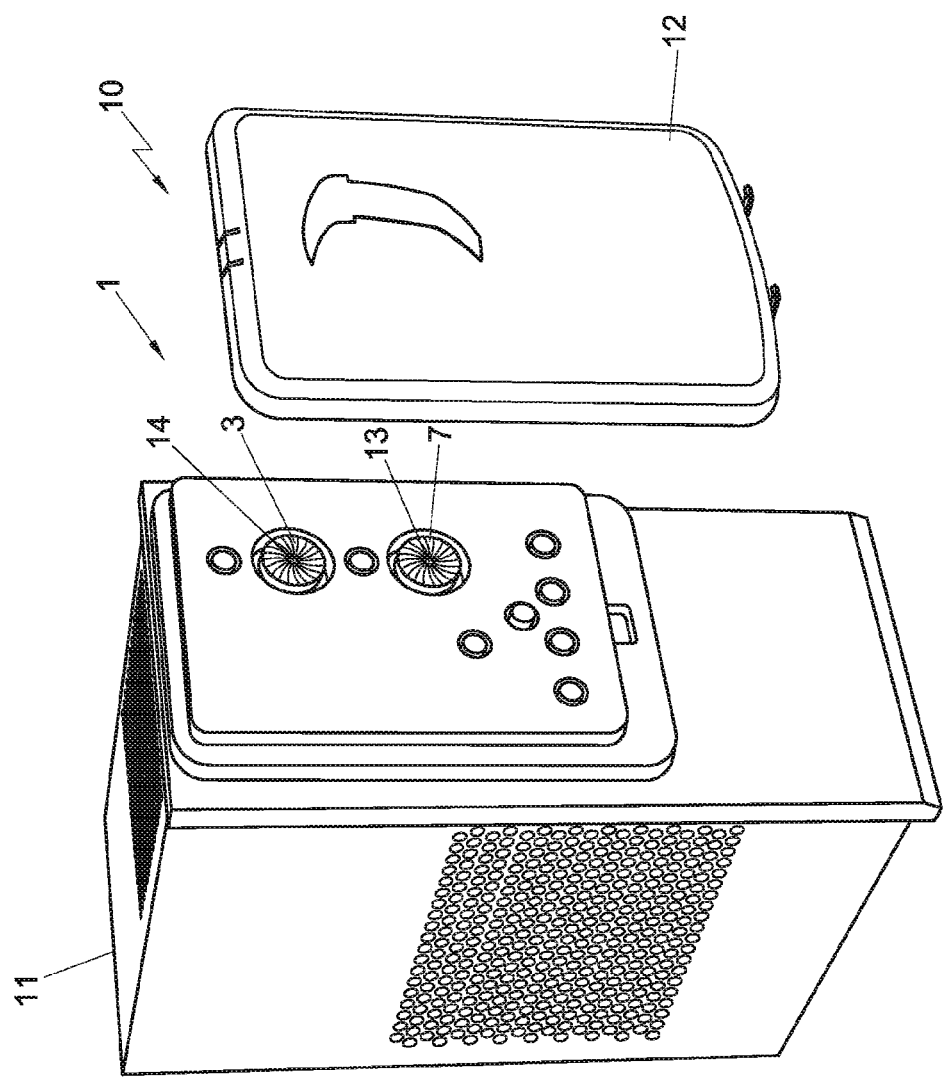
FIG. 2 shows a schematic perspective exploded view of an irrigation/aspiration system according to the invention.

FIG. 2 shows a schematic perspective view of a pump system 10 according to the invention. In particular, FIG. 2 shows an embodiment of an irrigation/aspiration system 10 for use in surgical applications, such as for small incision surgery in for example the eye. The irrigation/aspiration system 10 is then arranged for irrigating and aspirating a surgical site.

The pump system 10 comprises in this embodiment two main parts, a pump unit 11 and a cartridge 12. The pump unit 11 and the cartridge 12 are shown at a distance from each other, but are in operation coupled to each other. Typically, the pump unit 11 forms part of a larger entity such as a surgical operating machine. Such a machine is usually provided in an operating room.

The pump system 10 comprises a pump 1, more specifically in this embodiment, a membrane pump 1. The membranes of the membrane pump 1 are provided in the cartridge 12 and the plunger elements are provided on the pump unit 11. In coupled state, they work together to form the pump 1. The pump 1 functions as explained in relation to FIG. 1a-FIG. 1d.

In FIG. 2 the pump plunger elements 3, 7 are visible. Here, the pump plunger elements 3, 7 are arranged to provide an underpressure between a membrane body and the pump plunger element 3, 7. Thereto, the pump plunger element 3, 7 is provided with a small bore 13, 14 approximately in the centre of the pump plunger element 3, 7. Through this bore 13, 14 an underpressure is created between the membrane body and the pump plunger element such that the membrane body is sucked against the pump plunger element. Thus, by moving the pump plunger element, the membrane body is moved as well, thereby the volume of a pump chamber can be varied.

Figure 3:
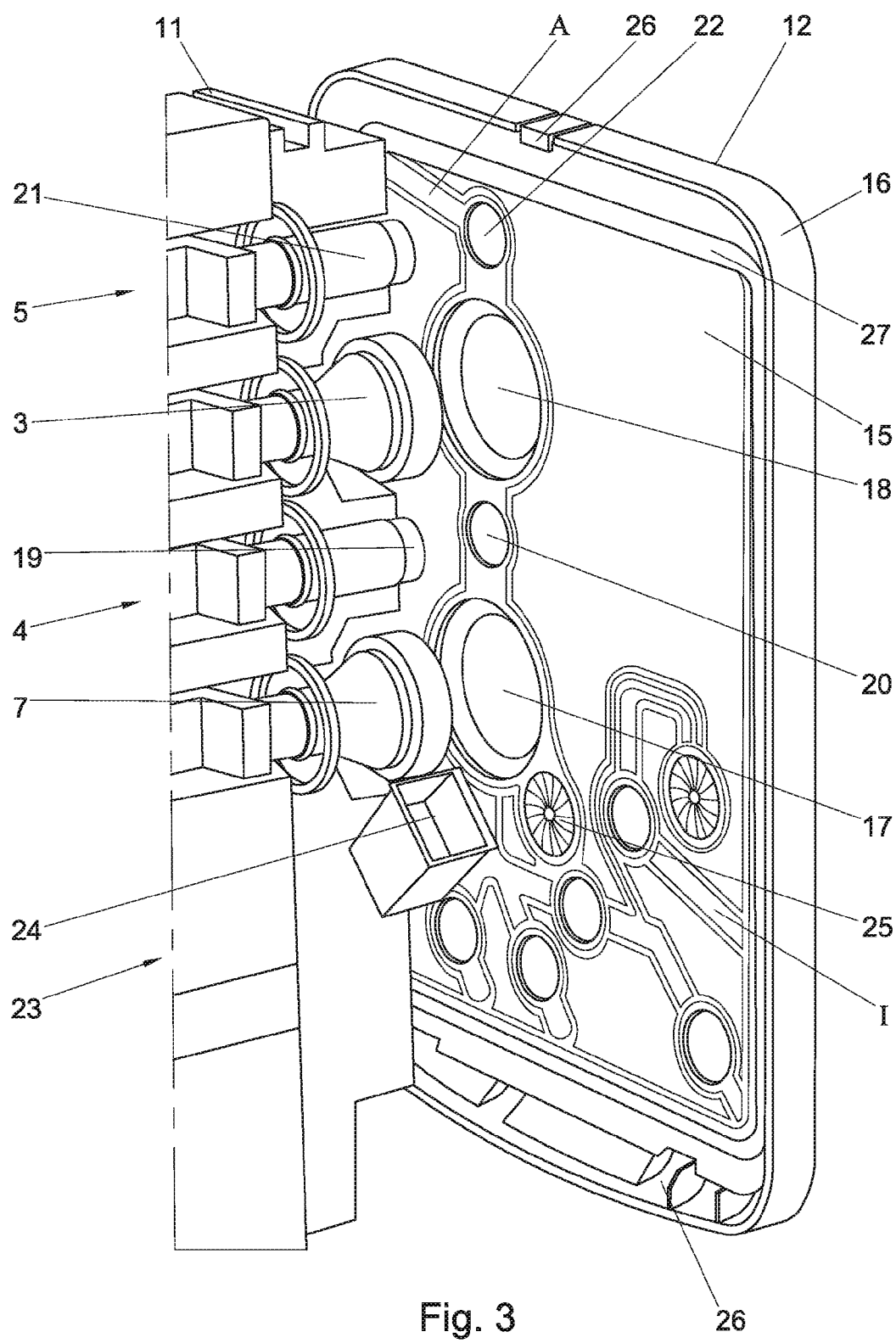
FIG. 3 shows a schematic perspective rear view of part of the pump unit and of the cartridge according to the invention.

FIG. 3 shows a perspective rear view of the surgical cartridge 12 at a distance of part of the pump unit 11. The surgical cartridge 12 comprises an inner plate 15 and an outer plate 16. The outer plate 16 is arranged approximately parallel to the inner plate 15 such that between the inner plate 15 and the outer plate 16 flow paths I, A can be arranged. The flow paths I, A are better visible in FIG. 5 and FIG. 6. The outer plate 16 is preferably made from relatively rigid plastic material, as well as the inner plate 15. Advantageously, they are welded together.

Figure 6:
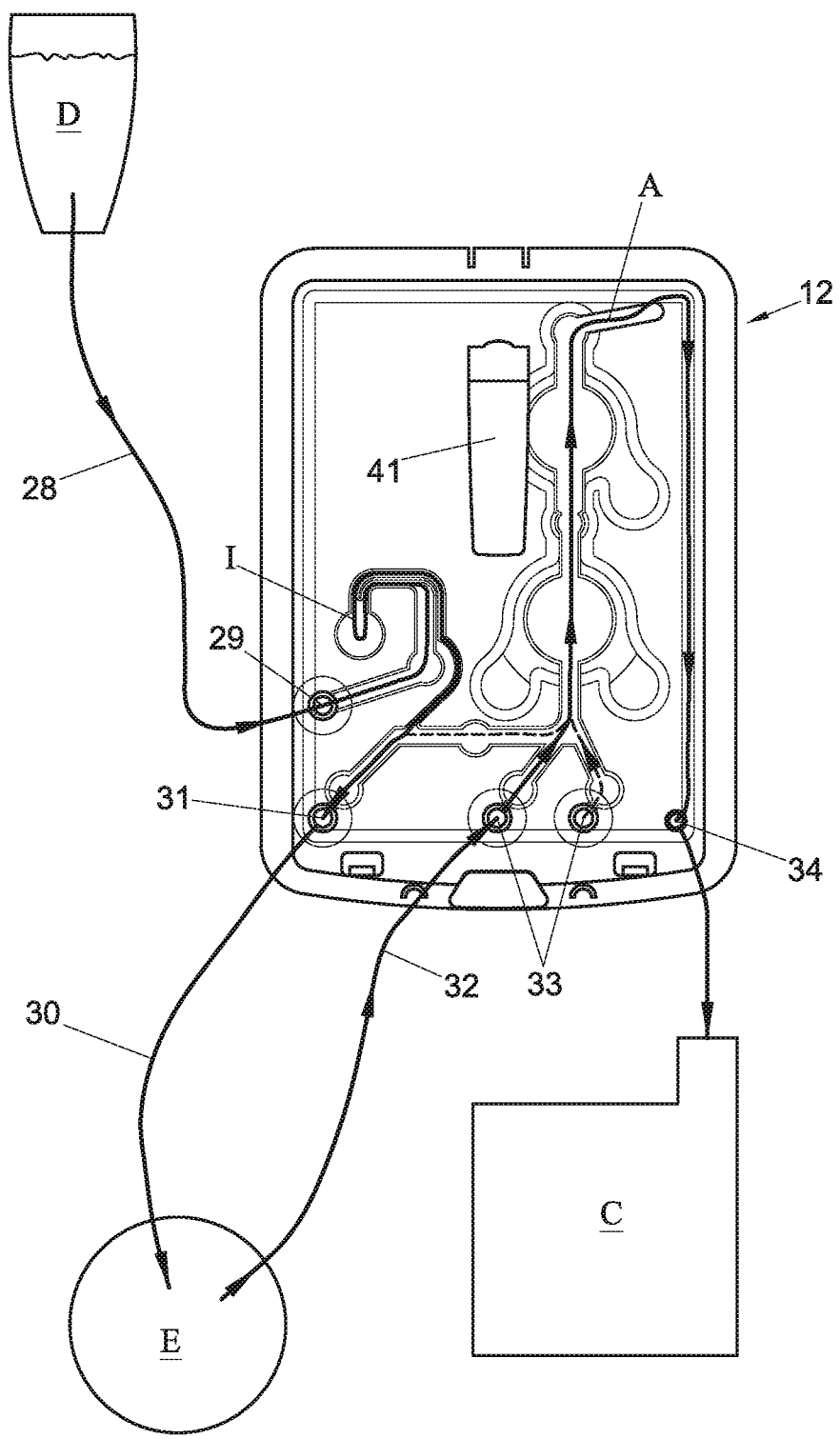
FIG. 6 shows a schematic front view of a cartridge according to the invention showing the fluid flow from infusion bag to collection bag.

Further, the inner plate 15 is provided with relatively flexible elements forming membrane bodies. An auxiliary membrane body 17 and a main membrane body 18 are provided that cooperate with auxiliary pump plunger element 7 and main pump plunger element 3 respectively. First and second valves 4, 5 comprise a first valve element 19 and a first valve body 20 and a second valve element 21 and a second valve body 22 respectively. The valve bodies 20, 22 are membrane bodies and are flexible as compared to the rigid inner plate 15. An embodiment of the valve construction is shown in FIG. 6.

The pump system 10 further comprises at least one pressure sensor 23. Here, the pressure sensor 23 comprises a pressure element 24 and a membrane pressure body 25. The membrane pressure body 25 is in fluid contact with the fluid flow path I, A and the pressure element 24 then measures the force and/or displacement of the membrane pressure body 25 as to establish the pressure in the fluid flow path I, A. Advantageously, the membrane pressure body 25 is arranged in the fluid flow path I, A. The membrane pressure body 25 has an inner side which is in contact with the fluid flowing through the flow path I, A and has an outer side facing away from the fluid flow path I, A at the outside of the fluid flow path I, A. The outer side of the membrane pressure body 25 is in contact with the pressure element 24. The pressure element 24 therefore does not form part of the cartridge 12, but can be arranged in for example the pump unit 11, as in this example.

Of course, in relation to other cartridges the pressure element 24 can be arranged elsewhere on the operating machine for cooperation with the pressure membrane body 25. The cartridge 12 can thus be more lightweight and/or more cost effective and/or more thin when the pressure sensor can be omitted. Also, since the cartridge 12 is a disposable article, a relative expensive pressure sensor does not have to be thrown away together with the cartridge 12, but can remain on the pump unit for use with a subsequent cartridge 12. This is contrary to the prior art wherein the pressure sensor forms part of the disposable cartridge.

According to an aspect of the invention, the pressure element 24 is a load cell element that can measure the displacement of the pressure body membrane 25 and translate the measured displacement into a force value.

The surgical cartridge 12 further comprises coupling elements 26 that are arranged for cooperation with coupling elements, not shown here, on the pump unit 11. The cartridge 12 typically is a one-way or throw-away product, while the pump unit 11 remains. The cartridge 12 can then be coupled before use to the pump unit 11 and after the surgical use, the cartridge 12 can be removed from the pump unit 11 and be thrown away. Also, by providing the cartridge 12 as a throw-away article, the cartridge 12 can easily be sterilised.

The cartridge 12 is in this embodiment also provided with a sealing edge 27 for sealingly couple to the pump unit 11. When connecting the cartridge 12 to the pump unit 11 via the coupling elements 26, a space is created between the inner plate 15 and the pump unit 11 which the sealing edge 27 sealingly closes off. This space can then be provided with an underpressure such that the cartridge 12 is being sucked towards the pump unit 11. This underpressure in fact provides for a firm, and additional to the coupling elements 26, connection of the cartridge 12 to the pump unit 11. The cartridge 12 is firstly coupled to the pump unit 11 via the coupling elements 26 to provide for initial coupling and/or centring of the cartridge 12 with respect to the pump unit 11. Then, secondly, the space between the inner plate 15 and pump unit 11 is set to an underpressure that may be in range of approximately 15-75 mmHG absolute pressure to firmly fixate the cartridge 12 to the pump unit 11 during the operation. This firm fixation may allow more accurate actuation of the plunger elements 3, 7 and/or the valve elements.

Figure 4:
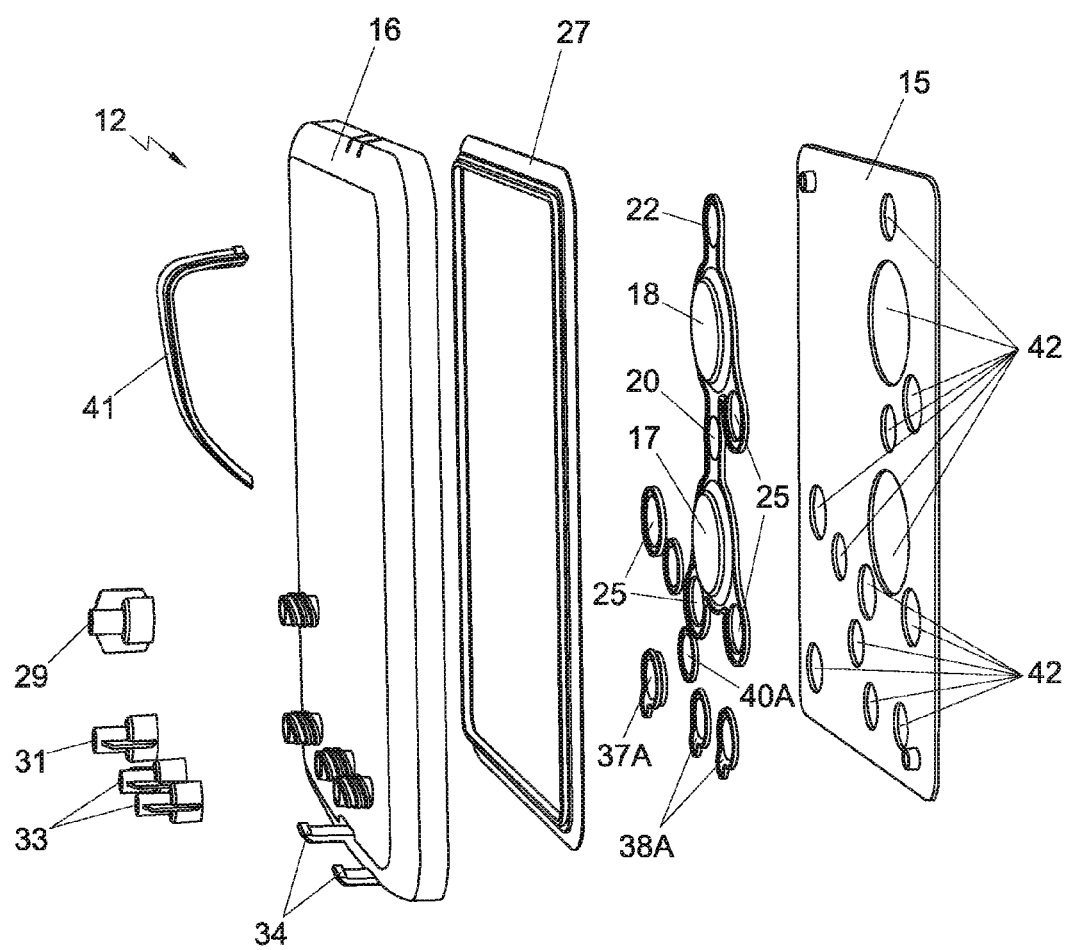
FIG. 4 shows a schematic exploded view of a cartridge according to the invention.

FIG. 4 shows a schematic perspective exploded view of the cartridge 12 according to the invention. The inner plate 15 and the outer plate 16 are usually made from relatively hard plastic material and can be welded together. It can be seen that the outer plate 16 is provided with ribs forming the flow paths I, A once the outer plate 16 is engaged with the inner plate 15. In the inner plate 15, cut-aways 42 are provided in which flexible membranes fit. The membranes, here pressure membrane bodies 25, valve membrane bodies 22, 20, 37A, 38A and 40A, membrane bodies 17, 18, are usually made from a flexible, elastic material, e.g. an elastic thermoplastic material. The membranes face at one side, the inner side, the flow path and form in this embodiment part of the wall of the flow path, and face at another side, the outer side, away from the flow path. The membranes are with their inner side in fluid contact with the fluid flowing through the flow path and are with their outer side in contact with the plunger element or valve element operating them.

The sealing edge 27 allows to vacuum couple the cartridge 12 to the pump unit 11. Further, the outer plate 16 is provided with a handle bar 41 for manually maneuvering the cartridge 12.

In addition, the connections, 29, 31, 33, for the flow lines are provided at the outer plate 16. Further, connections 34 are provided to hang a collection bag C onto.

A person wanting to use the cartridge 12 will grab it at the handle bar 41 and will first couple it with the coupling elements 26 to the pump unit 11. Then the underpressure can be provided to vacuum couple the cartridge 12 to the pump unit 11. The coupling elements thus provide for additional safety, because in case of power shutdown, the underpressure dissolves and thus the vacuum coupling is undone. However, due to the coupling elements 26, the cartridge 12 remains coupled to the pump unit 11, so a safe situation remains.

Figure 5:
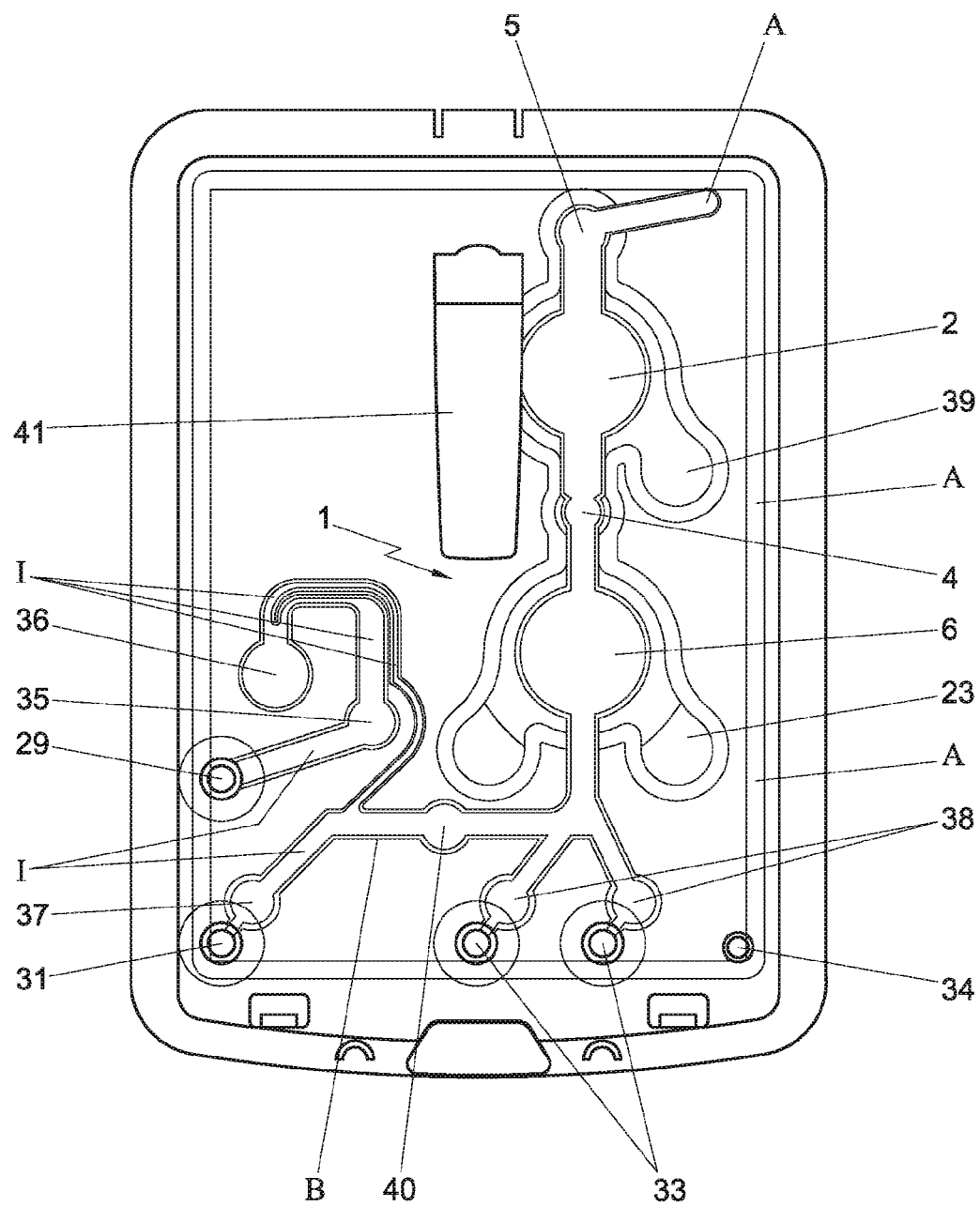
FIG. 5 shows a schematic front view of a cartridge according to the invention.

FIG. 5 and FIG. 6 show a schematic front view of the cartridge 12 according to the invention, wherein in FIG. 5 also the flow path is indicated.

From an infusion bag D an infusion line 28 goes to the cartridge 12. The infusion line 28 is connected to the cartridge at the infusion line connection 29. Then, the fluid flows through the irrigation path I in the cartridge 12 towards the eye E. Between the irrigation flow path I and the eye E, the irrigation line 30 is provided. The irrigation line 30 is connected to the cartridge at the irrigation connection 31. From the eye E to the cartridge 12, there is an aspiration line 32 to aspirate the fluid from the eye E. The aspiration line 32 is connected to the cartridge at the aspiration connection 33. In this embodiment, the aspiration connection 33 is provided twice. Then the fluid flows into the aspiration flow path A in the cartridge 12 towards the collection bag C. The collection bag C is connected to the cartridge at least at the collection bag connection 34. The fluid may then flow directly into the collection bag or a collection bag line may be connected between the cartridge 12 which ends into the collection bag.

Following the fluid flow from the infusion connection 29 in the irrigation flow path I, the fluid passes an infusion valve 35 for opening/closing the fluid flow coming from the infusion bag D.

Then the fluid passes a pressure sensor 36 to determine the pressure in the irrigation flow path I. Prior to entering the irrigation line 30 via the irrigation connection 31, there is an irrigation valve 37 provided to open/close the irrigation line. Fluid aspirated from the eye E passes the aspiration valve 38 before flowing towards the pump 1. The pump 1 comprises, as set out in relation to FIG. 2, an auxiliary pump chamber 6, a first valve 4, a main pump chamber 2 and a second valve 5. Further, a pressure sensor 23 is provided to determine the pressure in the auxiliary pump chamber 6 and a pressure sensor 39 is provided to determine the pressure in the main pump chamber 2.

Between the irrigation flow path I and the aspiration flow path A, a backflush flow path B with a backflush valve 40. The backflush valve 40 can be opened when the surgeon may require additional fluid from the infusion bag D at the surgical site. This fluid can then enter the eye via the backflush flow path B and the aspiration line 32. The irrigation valve 37 is in that case closed and the pump 1 is then stopped to allow the backflush fluid towards the eye.

An advantage of the system 10 according to the invention, and in particular of the embodiment shown in FIG. 6, is that there will be fluid pressure onto the eye, also in case of a power shutdown. In case of a power shutdown, the pump is not functioning anymore and the valves will go to their open condition towards which they are pretensioned. At least the infusion valve 35 will remain in the open position. Since the infusion bag D is positioned higher than the eye E, fluid will flow from the infusion bag D towards the eye E along the open valves 35, 37. The pressure on the eye E will thus be somewhat higher than ambient pressure, i.e. ambient pressure and the pressure of the fluid column between the eye E and the infusion bag D. By keeping pressure onto the eye E, also in case of a power shutdown, there is, during operation, a safe situation.

Advantageously, a control unit is provided in the pump unit 11 to control the operation of the pump 1. Usually, the surgeon will prior or during the surgical operation give settings to the surgical machine, for example of the flow and/or underpressure required. These settings are then inputted to the control unit which then controls the pump to obtain the required settings. Since pressure sensors are available, not only the flow in the system 10 is known, but also the pressure such that the system 10 can operate both as a flow controlled system as well as a pressure controlled system. The system 10 can thus easily be operated as a flow controlled system or as a pressure controlled system, since switching between both operating modes is a mere setting in the control unit. In addition the system 10 has relative short response times.

For example, by providing the pressure sensor 39 in addition to the pressure sensor 23, the pressure values of both sensors 39, 23 can be compared by the control unit. The control unit may then operate the valve 4 between the pump chambers 6, 2 only when the pressure in both pump chambers 6, 2 is equal, such that only controlled flow between both chambers 6, 2 is provided to obtain a flow as smooth as possible out of the eye E.

Figure 7A:
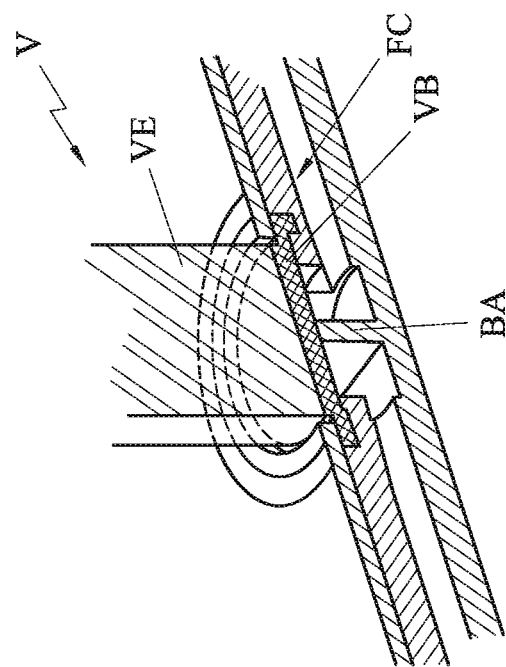
FIG. 7a and FIG. 7b show in a schematic perspective cross-sectional view the construction of a valve, in open and closed condition respectively, according to an aspect of the invention.
Figure 7B:
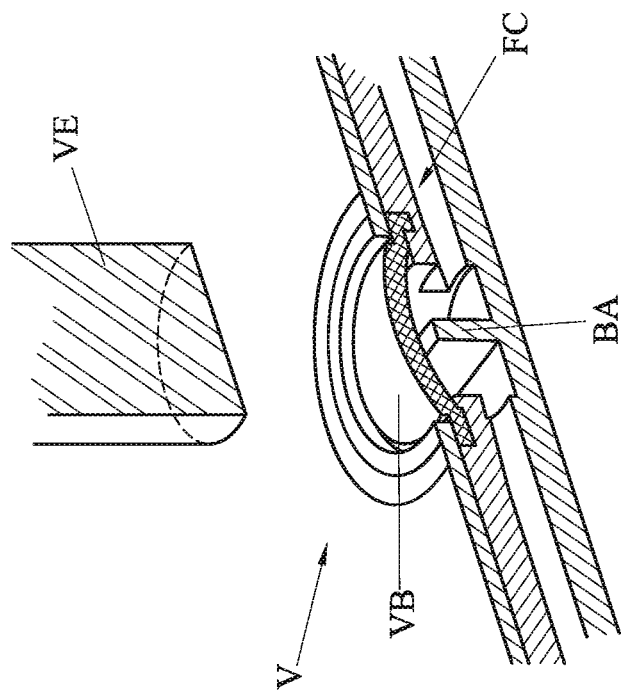

FIGS. 7A and 7B show schematically the construction of a valve V according to the invention. FIG. 7A shows the valve V in open condition and FIG. 7B shows the valve V in closed condition. The construction of the valve V can be considered as another aspect of the invention. Valves 4, 5, 35, 37 or 38 can be constructed according to the valve construction shown in FIG. 7. Valve V comprises a valve body VB and a valve element VE. The valve element VE operates the valve body VB. According to the invention, the valve body VB is a membrane body which is flexible and pretensioned towards the open condition. In the open condition, the valve body VB is concave. In a flow channel FC, such as the flow path A of the system 10, a baffle plate BA is provided. Typically, the baffle plate BA is approximately as high as the height of the flow channel FC. Due to the concave valve body VB, there is a distance between an upper side of the baffle plate BA and the valve body VB such that the flow channel FC is open in the open condition of the valve V and fluid can pass along the baffle plate BA. In the closed condition of the valve V, as shown in FIG. 6*b*, the valve element VE operates the valve body VB and presses the valve body VB against the baffle plate BA to close the flow channel FC. By moving the valve element VE, for example, a plunger element, upwards and downwards the valve body VB can be operated. The valve body VB can thus be pressed against the baffle plate BA to close the flow channel FC or be released from the baffle plate BA to open the flow channel FC. Advantageously, the valve element VE is provided in the system 10 according to the invention and/or is being operated by the control unit of the system 10.

According to a further aspect of the invention, the connections 29, 31 and 33 are all three different connections. Preferably, the connections 29, 31, 33 have different colours, and more preferably, are of different construction. The connections are arranged such that the infusion flow line 28 can only connect to the infusion connection 29 and does not fit to the other connections 31, 33. Also, the irrigation flow line 30 can only connect with the irrigation connection 31 and not with the other connections 29, 33. Also, the aspiration flow line 32 can only connect with the aspiration connection 33 and not with the other connections 29, 31. This allows minimizing of mistakes and a more safe and reliable operation of the system 10. By providing each of the connections 29, 31, 33 of a different size and/or construction and/or of a different colour, that corresponds with the construction and/or colour of the connection of the flow line mistakes in connecting the flow lines to the connection points may be minimized and preferably avoided. This may result in a more failure free operation of the system 10 and/or of the surgical operating machine. The valve construction may be considered as an invention on its own as well.

Many variants will be apparent to the person skilled in the art. All variants are understood to be comprised within the scope of the invention defined in the following claims.

What is claimed is:

1. An irrigation/aspiration system for irrigating and aspirating a surgical site comprising:
    an irrigation flow path for directing fluid towards the surgical site via an irrigation connection; and
    an aspiration flow path for directing fluid away from the surgical site via an aspiration connection,
    wherein in the aspiration flow path a membrane pump is arranged for pumping fluid through the aspiration flow path, and
    wherein the membrane pump comprises a main pump chamber, at least two valves including a first valve and a second valve for opening and/or closing the main pump chamber and, an auxiliary pump chamber having both its input and its output connection arranged between the aspiration connection and the main pump chamber for compensating movement of a main pump plunger element in the main pump chamber to provide for an approximately even fluid flow from the surgical site, and
    wherein the main pump chamber is arranged with the auxiliary pump chamber in series along the aspiration flow path,
    wherein the first valve is located between the main pump chamber and the auxiliary pump chamber, and the second valve is located downstream from the main pump chamber in the aspiration flow path,
    wherein the second valve is configured to be closed when the main pump plunger element moves upwardly to open the aspiration flow path such that the fluid is smoothly pumped out of the surgical site towards the main pump chamber and the auxiliary pump chamber.

2. The irrigation/aspiration system according to claim 1, wherein the auxiliary pump chamber is arranged with an auxiliary pump plunger element.

3. The irrigation/aspiration system according to claim 1, further comprising a control unit adapted to control the operation of the membrane pump.

4. The irrigation/aspiration system according to claim 1, further comprising a pressure sensor adapted to establish the pressure in the system.

5. The irrigation/aspiration according to claim 1, wherein the membrane pump comprises plunger elements that are arranged to provide an underpressure between a membrane body and a plunger element.

6. The irrigation/aspiration according to claim 1, comprising a cartridge in which the irrigation flow path and the aspiration flow path are arranged and a pump unit for cooperation with the cartridge.

7. The irrigation/aspiration system according to claim 6, wherein the cartridge is provided with rigid irrigation and aspiration flow paths in which membrane bodies are arranged that are adapted for cooperation with plunger elements of the pump unit.

8. The irrigation/aspiration system according to claim 6, wherein the cartridge is provided with a sealing edge for sealingly coupling to the pump unit.

9. The irrigation/aspiration system according to claim 8, wherein the cartridge is sealingly couplable to the pump unit by means of an underpressure.

10. The irrigation/aspiration system according to claim 6, wherein the cartridge is provided with coupling elements that are arranged for cooperation with coupling elements on the pump unit.

11. A method for controlling the irrigation/aspiration system according to claim 1, comprising:
    operating the auxiliary pump chamber in antiphase with respect to the main pump chamber to provide for an approximately smooth flow.

12. The irrigation/aspiration system according to claim 1, wherein the membrane pump further comprises an auxiliary pump plunger element,
    wherein the auxiliary pump plunger element is configured to move downwardly to the auxiliary pump chamber when the second valve is closed,
    wherein a speed of the auxiliary pump plunger element moving downwardly is slower than a speed of the main pump plunger element moving upwardly such that the fluid is smoothly pumped out of the surgical site towards the main pump chamber and the auxiliary pump chamber.

13. The irrigation/aspiration system according to claim 1, wherein the membrane pump further comprises an auxiliary pump plunger element, a main membrane body, and an auxiliary membrane body, and
    wherein the main pump plunger element is arranged to provide an underpressure between the main membrane body and the main pump plunger element, and the auxiliary pump plunger element is arranged to provide an underpressure between the auxiliary membrane body and the auxiliary pump plunger element.

* * * * *